US00PP10600P

United States Patent [19]

Janssen

[11] Patent Number: Plant 10,600

[45] Date of Patent: Sep. 8, 1998

[54] DRACAENA PLANT NAMED 'RIKI'

[75] Inventor: Cees Janssen, Honselersdijk, Netherlands

[73] Assignee: FA. Gebr. Janssen, Honselersdijk, Netherlands

[21] Appl. No.: 870,006

[22] Filed: Jun. 6, 1997

[51] Int. Cl.[6] ..... A01H 5/00

[52] U.S. Cl. ..... Plt./88.11

[58] Field of Search ..... Plt./88.11

[56] References Cited

PUBLICATIONS

Huxley et al.; The New Royal Horticultural Society Dictionary of Gardening; vol. 2, pp. 96–97; 1992.

*Primary Examiner*—James R. Feyrer
*Assistant Examiner*—Kent L. Bell
*Attorney, Agent, or Firm*—C. A. Whealy

[57] ABSTRACT

A distinct cultivar of Dracaena plant named 'Riki', characterized by its upright and outwardly arching growth habit; striking dark green and yellowish green variegated leaves that are thick, strong and leathery; and excellent post-production longevity.

2 Drawing Sheets

The present invention relates to a new and distinct cultivar of Dracaena plant, botanically known as *Dracaena reflexa*, and hereinafter referred to by the cultivar name 'Riki'.

The new cultivar was discovered by the inventor in Honselersdijk, The Netherlands, as a naturally-occurring mutation of the nonpatented Dracaena cultivar Song of India, and was observed as a single plant in a group of plants of the parent cultivar in September, 1993.

Asexual propagation of the new cultivar at Honselersdijk, The Netherlands, has shown that the unique features of this new Dracaena plant are stable and reproduced true to type in successive generations of asexual propagation.

The new Dracaena has not been observed under all possible environmental conditions. The phenotype may vary somewhat with variations in environment such as temperature and light intensity, without, however, any variance in genotype. The following observations, measurements and comparisons describe plants grown in Honselersdijk, The Netherlands, in a glass greenhouse with day and night temperatures ranging from 19 to 23° C and light levels of about 2,000 to 3,000 footcandles.

The following traits have been repeatedly observed and are determined to be the unique characteristics of 'Riki' . These characteristics in combination distinguish 'Riki' as a new and distinct cultivar:

1. Upright and outwardly arching growth habit.
2. Striking dark green and yellowish green variegated leaves that are thick, strong and leathery.
3. Excellent post-production longevity.

The new Dracaena can be compared to its parent cultivar, the cultivar 'Song of India'. The new cultivar is different from plants of 'Song of India' and other Dracaenas commercially known and used in commerce in the following characteristics:

1. Plants of the new Dracaena have a striking and intense leaf variegation pattern compared to other Dracaenas. The dark green portions are darker and yellowish green areas are lighter on plants of the new Dracaena compared to plants of the cultivar 'Song of India'.
2. Plants of the new Dracaena have thicker leaves than other Dracaenas. The thicker leaf imparts greater sucking insect resistance to plants of the new Dracaena compared to plants of the cultivar 'Song of India'.
3. Root development on plants of the new Dracaena is more rapid than plants of the selection 'Song of India'.

The accompanying colored photographs illustrate the overall appearance of the new cultivar, showing the colors as true as it is reasonably possible to obtain in colored reproductions of this type.

The first photograph comprises a top perspective view of a typical potted plant of 'Riki'.

The second photograph comprises a close-up view of a leaf of 'Riki' showing the variegation pattern. Leaf colors in the photographs may appear different from the actual colors due to light reflectance.

In the following description, color references are made to The Royal Horticultural Society Colour Chart except where general terms of ordinary dictionary significance are used.

Botanical Classification: *Dracaena relfexa* cultivar 'Riki'.

Parentage: Naturally-occurring mutation of the nonpatented Dracaena cultivar 'Song of India'.

Propagation:

*Method.*—By cuttings.

*Time to initiate roots.*—42 and 70 days during the summer and winter, respectively.

*Rooting habit.*—Numerous, thick, and fleshy roots.

Plant Description:

*Plant shape.*—Upright, inverted triangle, symmetrical.

*Growth habit.*—Erect when young, becoming outwardly arching as leaves develop. Appropriate for 15 to 27-cm containers.

*Plant height.*—40 to 50 cm from soil level to top of leaf plane.

*Plant vigor.*—Moderate.

*Growth rate.*—Slow.

*Crop time.*—About 10 months are usually required from planting of a young plant to a finished plant in a 15-cm container.

*Foliage description.*—Quantity of leaves per finished plant: About 20 to 25. Leaf shape: Linear. Leaf apex: Apiculate. Leaf base: Broadens at the base. Leaf margin: Entire. Leaf texture: Leathery, smooth, glabrous. Leaf size: Length: About 40 cm. Width: About 3 cm. Leaf color: Longitudinally variegated. Margins are dark green, 139A. Central area with dark to yellowish green longitudinal stripes, 139A, 144A or 144B.

Flower Description: Flowers have not been observed on plants of the new Dracaena.

Disease Resistance: Susceptibility nor resistance to pathogens common to Dracaenas has been observed.

Insect Resistance: Thickness of leaves, characteristic of the new Dracaena, imparts resistance to sucking insects.

It is claimed:

1. A new and distinct cultivar of Dracaena plant named 'Riki', as illustrated and described.

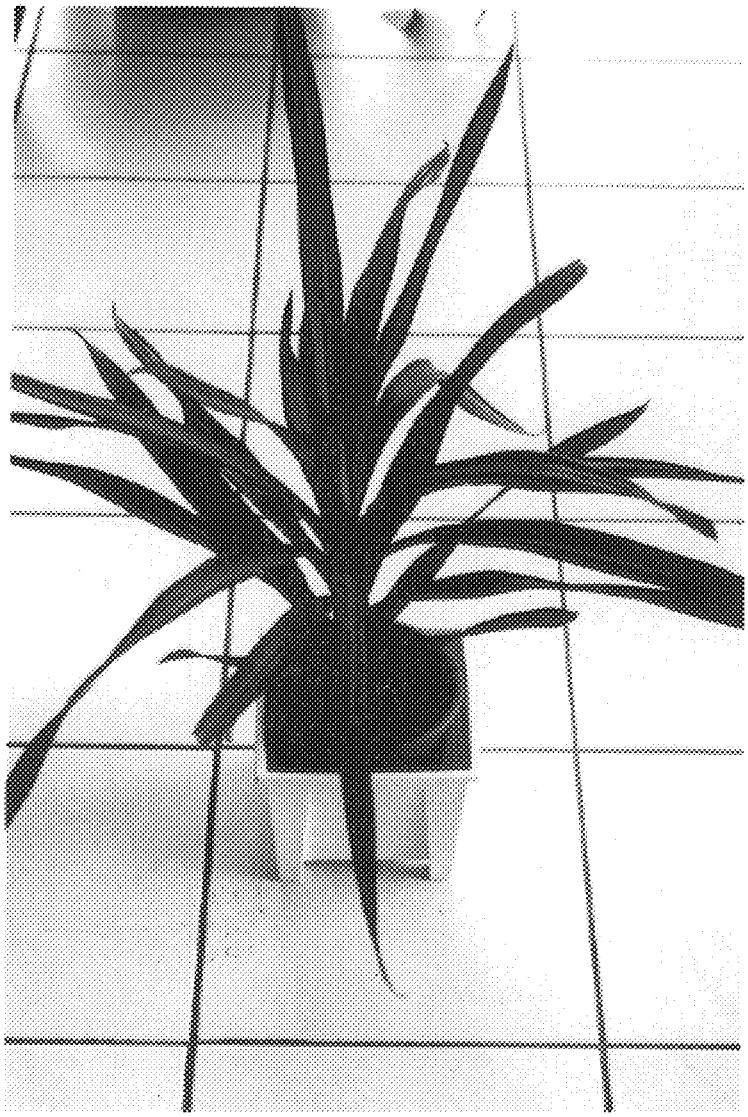

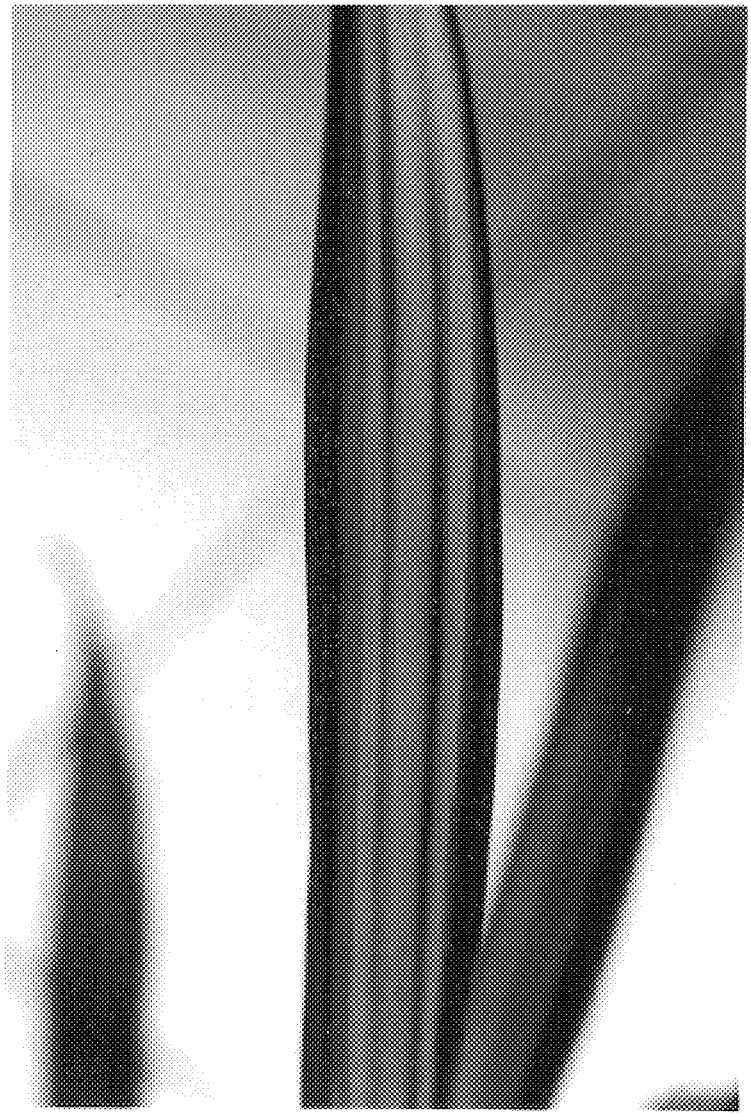

* * * * *